(12) United States Patent
Hoegele et al.

(10) Patent No.: US 10,473,905 B2
(45) Date of Patent: Nov. 12, 2019

(54) MICROSCOPE HAVING AN OPTICAL COHERENCE TOMOGRAPHY DEVICE

(71) Applicant: Carl Zeiss Meditec AG, Jena (DE)

(72) Inventors: Artur Hoegele, Oberkochen (DE); Franz Merz, Aalen (DE); Christian Beder, Aalen (DE); Andre Mueller, Koenigsbronn-Zang (DE); Daniel Kolster, Oberkochen (DE); Peter Reimer, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/165,724

(22) Filed: Oct. 19, 2018

(65) Prior Publication Data

US 2019/0155010 A1    May 23, 2019

(30) Foreign Application Priority Data

Oct. 20, 2017    (DE) .................. 10 2017 124 548

(51) Int. Cl.
*G02B 21/00* (2006.01)
*A61B 90/00* (2016.01)
(Continued)

(52) U.S. Cl.
CPC .......... *G02B 21/0032* (2013.01); *A61B 3/102* (2013.01); *A61B 90/36* (2016.02);
(Continued)

(58) Field of Classification Search
CPC .......... G02B 21/0012; G02B 21/0056; G02B 21/22; G02B 21/24; G02B 27/10;
(Continued)

(56) References Cited

U.S. PATENT DOCUMENTS

| 4,691,997 A | 9/1987 | Muchel |
| 7,488,070 B2 | 2/2009 | Hauger et al. |

(Continued)

FOREIGN PATENT DOCUMENTS

| DE | 3508306 A1 | 9/1986 |
| DE | 10202509 A1 | 7/2003 |

(Continued)

OTHER PUBLICATIONS

Decision to Grant of the German Patent Office dated Apr. 11, 2018 in German patent application 10 2017 124 548.0 on which the claim of priority is based.

(Continued)

*Primary Examiner* — Arnel C Lavarias
(74) *Attorney, Agent, or Firm* — Walter Ottesen, P.A.

(57) ABSTRACT

A microscope having an observation beam path including a main objective, an OCT device including a first detection beam path, a wavefront measuring device including a second detection beam path, a first, a second and a third optics group is provided, wherein the first detection beam path contains the main objective and the first to third optics group, and the first to third optics group forms an afocal imaging optical unit of the first detection beam path and the second detection beam path contains the main objective, the first optics group and the second optics group, and the main objective and the first and second optics group form an afocal imaging optical unit of the second detection beam path.

20 Claims, 8 Drawing Sheets

(51) Int. Cl.
*A61B 3/10* (2006.01)
*G01B 9/02* (2006.01)
*G02B 27/14* (2006.01)
*A61B 90/20* (2016.01)
*A61B 5/00* (2006.01)

(52) U.S. Cl.
CPC ..... *G01B 9/02091* (2013.01); *G02B 21/0012* (2013.01); *G02B 27/141* (2013.01); *A61B 5/0066* (2013.01); *A61B 5/0073* (2013.01); *A61B 90/20* (2016.02)

(58) Field of Classification Search
CPC .............. G02B 27/1006; G02B 27/141; G02B 21/0032; G02B 13/0095; G02B 21/00; G02B 21/0004; G02B 21/002; G02B 21/18; G02B 21/12; G02B 23/00; A61B 90/36; A61B 3/102; A61B 3/13; A61B 90/20; A61B 5/0066; A61B 5/0073; G01B 9/02091
USPC ....... 359/362, 368, 363, 369, 385, 388, 390, 359/399, 419, 423, 434, 435, 372, 373, 359/374, 375, 376, 377, 378
See application file for complete search history.

(56) References Cited

U.S. PATENT DOCUMENTS

| | | | |
|---|---|---|---|
| 7,845,798 B2 | 12/2010 | Kuebler et al. | |
| 7,889,423 B2 | 2/2011 | Reimer et al. | |
| 8,049,873 B2 * | 11/2011 | Hauger | A61B 3/102 356/73 |
| 8,459,795 B2 * | 6/2013 | Seesselberg | A61B 3/1015 351/205 |
| 9,560,963 B2 | 2/2017 | Buckland et al. | |
| 9,585,553 B2 * | 3/2017 | Zhou | A61B 3/0025 |
| 2003/0139736 A1 | 7/2003 | Sander | |
| 2007/0013918 A1 | 1/2007 | Hauger et al. | |
| 2008/0117503 A1 | 5/2008 | Reimer et al. | |
| 2008/0125763 A1 | 5/2008 | Amoldussen et al. | |
| 2009/0257065 A1 | 10/2009 | Hauger et al. | |
| 2010/0321675 A1 | 12/2010 | Huang et al. | |
| 2010/0324542 A1 | 12/2010 | Kurtz | |
| 2012/0069303 A1 | 3/2012 | Seesselberg et al. | |
| 2012/0082410 A1 | 4/2012 | Peng et al. | |
| 2012/0147460 A1 | 6/2012 | Kuebler et al. | |
| 2013/0131652 A1 | 5/2013 | Dick et al. | |
| 2013/0211391 A1 | 8/2013 | BenYakar et al. | |
| 2015/0031993 A1 | 1/2015 | Buckland et al. | |
| 2015/0077705 A1 | 3/2015 | Artsyukhovich et al. | |
| 2016/0360961 A1 | 12/2016 | Buckland et al. | |
| 2016/0365697 A1 | 12/2016 | Hori et al. | |
| 2017/0189228 A1 | 7/2017 | Yang et al. | |

FOREIGN PATENT DOCUMENTS

| | | |
|---|---|---|
| DE | 10360570 A1 | 7/2005 |
| DE | 102008047400 A1 | 4/2010 |
| DE | 102008063644 A1 | 7/2010 |
| DE | 112009000369 T5 | 1/2011 |
| DE | 102009037841 A1 | 2/2011 |
| DE | 102010024606 A1 | 12/2011 |
| EP | 1918756 A1 | 5/2008 |
| EP | 2585014 A2 | 5/2013 |
| EP | 3005938 A2 | 4/2016 |
| WO | 2008061034 A1 | 5/2008 |
| WO | 2010031540 A2 | 3/2010 |
| WO | 2011091283 A1 | 7/2011 |
| WO | 2014074636 A1 | 5/2014 |
| WO | 2015017375 | 2/2015 |
| WO | 2015042305 A1 | 3/2015 |
| WO | 2015130651 A1 | 9/2015 |

OTHER PUBLICATIONS

Benabid, F. et al., "Fiber for Fiber Lasers: Kagome PC fiber goes to extremes for ultrashort-pulse lasers", Sep. 8, 2014, copyright PennWell Corporation, Tulsa, OK, pp. 1 to 8.

"Liquid Crystal Switchable Mirror", KentOptronics, downloaded Feb. 15, 2019, "http://www.kentoptronics.com/specs/Transflector.pdf", 2 pages.

Kozak, I. et al., "Modern retinal laser therapy", Saudi Journal of Ophthalmology (2015) 29, pp. 137 to 146, Elsevier B.V. on behalf of Saudi Ophthalmological Society, King Saud University.

"LENSX^R Laser: The Complete Anterior Segment Cataract Surgical Experience", Surgical for US Professionals, https://www.myalcon.com/products/surgical/lensx-laser/, downloaded Sep. 26, 2018, 2 pages.

Ober, M., et al., "Retinal Laser: Past, Present, and Future Technological advancement flourished early on, then plateaued. What's in store next? Part 1 of 2", Retinal Physician, Jan. 1, 2009, 6 pages, https://www.retinalphysician.com/issues/2009/jan-feb/retinal-laserspas...

VisuMax-Femtosecond Laser Solutions—Cornea & RefractiveMedi . . . Zeiss, 1 page, downloaded on Sep. 26, 2018, https://www.zeiss.com/meditec/us/products/ophthalmology-optometry/...

Office action and English translation of the Office action of the German Patent Office dated Mar. 22, 2018 in German patent application 10 2017 124 548.0 on which the claim of priority is based.

* cited by examiner

MICROSCOPE HAVING AN OPTICAL COHERENCE TOMOGRAPHY DEVICE

CROSS REFERENCE TO RELATED APPLICATION

The present application claims the priority of German patent application No. 10 2017 124 548.0, filed Oct. 20, 2017, with the entire content of this application herewith being incorporated by reference.

FIELD OF THE INVENTION

The present invention relates to a microscope with an observation beam path including a main objective, wherein the microscope is embodied as a surgical microscope, in particular.

BACKGROUND OF THE INVENTION

There increasingly is a need in such microscopes and in such surgical microscopes, in particular, to carry out various diagnostics examinations (such as imaging methods or refractive measurements, for example) during surgery. However, the separate devices required to this end significantly adversely affect the work surroundings and the workflow during an operation, for example.

SUMMARY OF THE INVENTION

Proceeding therefrom, it is therefore an object of the invention to provide a microscope with an observation beam path including a main objective, which provides additional measurement functions and, at the same time, has a compact embodiment.

A microscope according to the invention can include an observation beam path including a main objective, an OCT device including a first detection beam path, a wavefront measuring device including a second detection beam path, and a first, a second and a third optics group. Since the first detection beam path contains the main objective and the first to third optics group and the second detection beam path contains the main objective and the first and second optics group, the same optical elements are consequently used in part for both detection beam paths, leading to a compact structure.

The afocal imaging optical unit of the first detection beam path can be embodied as a Kepler telescope, with the first and the second optics group together forming the objective lens and the third optics group forming the eyepiece. Objective lens and eyepiece are configured in such a way that their foci coincide.

In the same way, the afocal imaging optical unit of the second detection beam path can be embodied as a Kepler telescope, with the main objective and the first optics group forming the objective lens and the second optics group forming the eyepiece of the Kepler telescope. Further, the objective lens and eyepiece of the Kepler telescope can be embodied in such a way that their foci coincide.

One could also say that the two Kepler telescopes of the two detection beam paths are nested in one another.

Further, the two afocal imaging optical units of the two detection beam paths are embodied in such a way that an intermediate image plane of the first detection beam path lies between the second and third optics group.

A beam splitter, which separates the first and second detection beam path, can be arranged between the second and third optics group. The beam splitter can be embodied in such a way that a permanent separation is present, and so both detection beam paths can always be used for measurements. By way of example, this can be realized by a dichroic beam splitter, a beam splitter embodied as a partly transmissive mirror. Further, it is possible to embody the beam splitter in such a way that the light of the second detection beam path is reflected and the light of the first detection beam path is transmitted. To this end, the beam splitter can be embodied as a mirror which includes a hole in the region of the light of the first beam path or has a transparent embodiment. This can be realized well, in particular, if the intermediate image plane of the first beam path lies between the second and third optics group. Naturally, the beam splitter can also have a quasi-inverted form. In this case, only the light of the first detection beam path is reflected and the light of the second detection beam path is transmitted. To this end, the beam splitter is embodied as a small mirror which only reflects the light of the first beam path. This can be realized particularly advantageously if the intermediate image plane of the first detection beam path lies between the second and third optics group.

Further, the beam splitter can be embodied as a temporary beam splitter which can be switched into two states, wherein the light is transmitted in the first detection beam path in a first of the two states and the light is transmitted in the second detection beam path in a second of the two states. By way of example, this can be realized by a mirror with an electrochromic layer, which can be switched into a reflective and a transmissive state. Further, it is possible to provide a mirror which is positioned in the beam path between the second and third optics group in one of the two states and positioned outside of the beam path between the second and third optics group in a second state. Thus, a movable or displaceable mirror is provided. The movement can be a translational movement and/or a pivoting movement (or rotational movement).

Further, an aperture stop for the second detection beam path can be arranged between the first and second optics group.

Moreover, a beam splitter, via which illumination radiation for the wavefront measuring device is input coupled, can be arranged between the first and second optics group, wherein the illumination radiation is directed at a specimen to be examined by the microscope (or an object to be examined) via the first optics group and the main objective. As a result of this input coupling of the illumination radiation for the wavefront measuring device, the illumination radiation for the wavefront measuring device need not pass through the second optics group, too, and so advantageously fewer optical interfaces at which reflections may occur, which may have a disadvantageous effect on the wavefront measurement, have to be passed through.

Moreover, the microscope can include an illumination device, the radiation of which (for example, from the visible spectrum) can be input coupled between the first and second optics group via a beam splitter in such a way that the radiation is directed at the specimen to be examined via the first optics group and the main objective (and not via the second optics group). In particular, the illumination device can be embodied as a coaxial illumination.

In particular, the same beam splitter between the first and second optics group can be used to steer the illumination radiation of the wavefront measuring device and the radiation of the illumination device to the first optics group such that these radiations can be directed at a specimen to be examined through the first optics group and the main objective. Consequently, the first optics group and the main objective are used as common first partial optical unit.

A further beam splitter can be provided, the beam splitter superposing the radiation of the illumination device and the illumination radiation of the wavefront measuring device and steering these to the beam splitter arranged between the first and second optics group. Preferably, a second partial optical unit for the illumination radiation of the wavefront measuring device and a third partial optical unit for the radiation of the illumination device are provided in front of the further beam splitter in order to be able to provide the desired illumination properties, which differ for the illumination radiation for the wavefront measuring device and the radiation of the illumination device.

In particular, the further beam splitter can be arranged outside of the first detection beam path and/or outside of the second detection beam path. Further, the further beam splitter can be a constituent part of the illumination beam path of the OCT device and/or a constituent part of the illumination beam path of the wavefront measuring device. Preferably, the further beam splitter is a reflective element in the illumination beam path of the wavefront measuring device and a transmissive element in the illumination beam path of the OCT device. In particular, the further beam splitter can be a dichroic beam splitter.

Consequently, it is advantageous for the radiation of the illumination device if the radiation from the visual spectral range (400-700 nm) is imaged into a homogeneous and color-corrected illuminated field. This can be realized by achromatic-aplanar imaging of the light source at infinity. This is followed by achromatic imaging of the illuminated field stop into the object plane (color-corrected illuminated field edge).

A plane wave should be present in the focal plane of the microscope for the illumination radiation of the wavefront measuring device, which can lie in the near infrared range (770-870 nm), for example. On the detection side, this wavefront should be imaged and detected in diffraction-limited fashion.

The first partial optical unit (main objective and first optics group) may impress aberrations on the radiation of the illumination device, although these can be corrected via the third partial optical unit in such a way that the demands on the illumination device are met.

Then, the second optics group is configured in such a way that the aberrations of the first partial optical unit are compensated for the wavefront measurement. It was found that a sufficiently good correction can be achieved, despite the high demands on the wavefront measurement.

The second detection beam path can pass through the main objective off-center (and optionally pass off-center through the first and second optics group). As a result, an illumination reflection stop for the illumination device can be positioned at the ideal location in the illumination device.

In the case of the off-center second detection beam path, it is advantageous to arrange an aperture stop between the first and second optics group as a delimitation for the evaluation pupil of the wavefront. Further, a long-pass filter for the wavefront measurement wavelength and the OCT measurement wavelength for the suppression of stray light can be arranged downstream of the beam splitter in the detection direction, the beam splitter being arranged between the first and second optics group.

In particular, the illumination device can be embodied in the same way as the illumination device 120 in U.S. Pat. No. 7,889,423. Here, reference is made, in particular, to FIGS. 1 to 5 with the associated description.

In particular, the microscope can be embodied as a stereo microscope with two observation beam paths (for example, optical observation beam paths). Further, the microscope can include an eyepiece in the observation beam path (or in each observation beam path). Further, the microscope can be embodied as a surgical microscope; preferably as a surgical microscope for eye surgery.

In a microscope according to the invention, the first and second detection beam path can pass off-center through the main objective (and optionally through the first, second and/or third partial optical unit). As a result, for example, an illumination reflection stop for the coaxial illumination can be positioned at the ideal location.

It goes without saying that the aforementioned features and those yet to be explained below can be used not only in the combinations specified but also in other combinations or on their own, without departing from the scope of the present invention.

The invention will be explained in more detail below on the basis of exemplary embodiments, with reference being made to the attached drawings, which likewise disclose features essential to the invention. These exemplary embodiments serve merely for illustration and should not be interpreted as restrictive. By way of example, a description of an exemplary embodiment with a multiplicity of elements or components should not be interpreted to the effect that all these elements or components are necessary for implementation purposes. Rather, other exemplary embodiments also may contain alternative elements and components, fewer elements or components or additional elements or components. Elements or components of different exemplary embodiments can be combined with one another, unless indicated otherwise. Modifications and developments which are described for one of the exemplary embodiments may also be applicable to other exemplary embodiments. In order to avoid repetition, the same elements or corresponding elements in the various figures are denoted by the same reference signs and are not explained a number of times.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
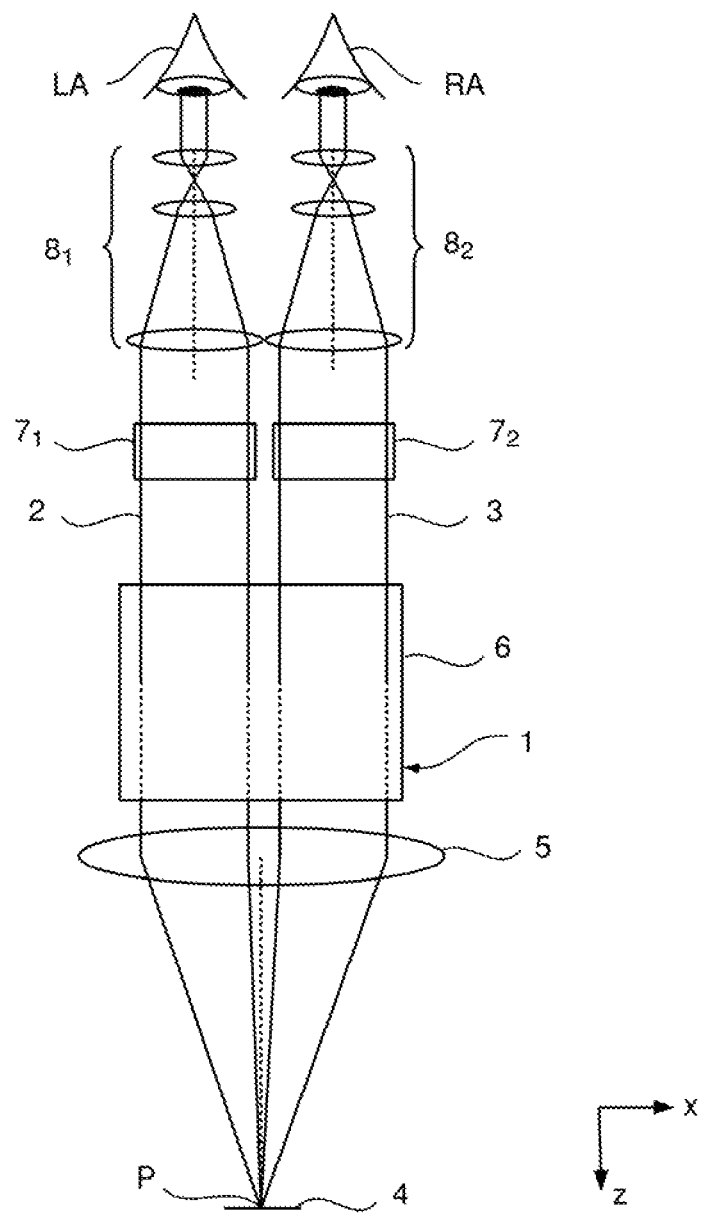
FIG. 1 shows a schematic illustration of an exemplary embodiment of the microscope 1 according to the invention.

The two optical observation beam paths 2, 3 of a microscope 1 according to the invention, which is embodied here as a stereo surgical microscope 1, are shown schematically in FIG. 1. The beam paths extend from an object 4 to be observed, through a main objective 5, then through a first beam splitter 6, a zoom optical unit 7₁, 7₂ and an eyepiece-tube optical unit 8₁, 8₂ (which is also referred to as eyepiece 8₁, 8₂ below), such that an observer can perceive the object to be observed in magnified fashion using their eyes RA, LA.

The microscope 1 further includes an OCT device 10 (OCT=optical coherence tomography), a wavefront measuring device 11 and an illumination device 12, the illumination beam paths of which are deflected by the first beam splitter 6 to the main objective 5, and so these pass through the main objective 5, and the detection beam paths of which pass through the main objective 5 and are deflected by the first beam splitter 6. For the purposes of simplifying the illustration, the OCT device 10, the wavefront measuring device 11 and the illumination device 12 are not plotted in FIG. 1. Their configuration and their arrangement are illustrated in the plan view of FIG. 2 and the side view of FIG. 3, with the optical observation beam paths 2, 3 only being indicated schematically in these views.

In addition to the main objective 5 and the first beam splitter 6, the OCT device 10 includes a first optics group 13, a second optics group 14, a third optics group 15, a scanning unit 16, a collimator optical unit 17, a light guide 18 and an OCT module 19.

The wavefront measuring device 11 includes the main objective 5, the first beam splitter 6, the first optics group 13, a second beam splitter 20, an aperture stop 21, the second optics group 14, a third beam splitter 22 and a wavefront sensor 23 (for example, a Shack-Hartmann camera 23) for detection purposes. Further, the wavefront measuring device 11 includes an illumination laser 24, which emits laser radiation with a wavelength of 785 nm, a fourth optics group 25, a fourth beam splitter 26, the second beam splitter 20, the first optics group 13, the first beam splitter 6 and the main objective 5 for illumination purposes.

The illumination device 12 includes a light source 27, which emits illumination radiation in the range of 400 to 700 nm, a fifth optics group 28, the fourth beam splitter 26, the second beam splitter 20, the first optics group 13, the first beam splitter 6 and the main objective 5.

As is yet to be described in detail below, a Kepler telescope for the detection beam path of the OCT device 10 is formed via the first to third optics group 13-15 and a Kepler telescope for the detection beam path of the wavefront measuring device 11 is formed via the main objective 5 and the first and second optics group 13, 14, as a result of which both Kepler telescopes are nested in one another. As a result, a high integration and an installation-space-optimized construction can be realized.

Figure 4:
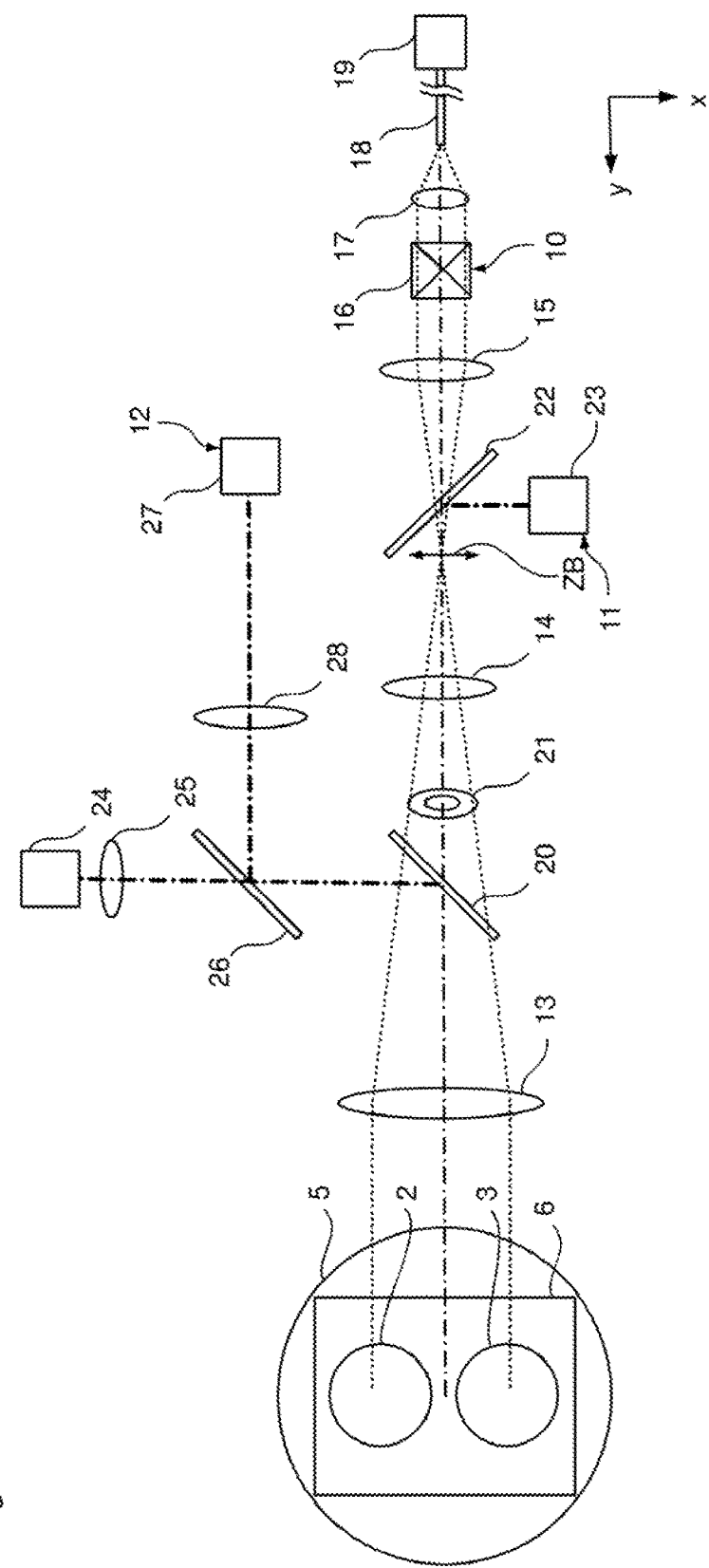
FIG. 4 shows a plan view as per FIG. 2, wherein an OCT beam is plotted in the field center (not scanned)

In FIG. 4, the aperture beam path of the OCT device 10 is plotted for a beam that is focused on the point P (FIG. 1) of the object 4 to be observed (the point P is the intersection of the optical axis of the main objective 5 and the focal plane in which the object 4 to be observed lies). As is clear from the plotted beam path, the first and second optics group 13, 14 form the objective lens of the Kepler telescope and the third optics group 15 forms the eyepiece of the Kepler telescope. One could also say that the first to third optics group 13 to 15 forms an afocal imaging optical unit for the OCT device 10.

During operation, the OCT module 19 produces the necessary coherent illumination radiation, which is guided through the light guide 18 and collimated via the collimator optical unit 17. The scanning unit 16 carries out the necessary deflection in the x- and y-direction. The Kepler telescope formed by the first to third optics group 13 to 15 carries out afocal imaging of the beam, which is deflected by the first beam splitter 6 and focused via the main objective 5.

The detection beam path is passed through in the opposite direction in the same way. Then, the detected radiation is guided to the OCT module 19 via the light guide 18, the detection being effected in a known manner in the OCT module.

Figure 5:
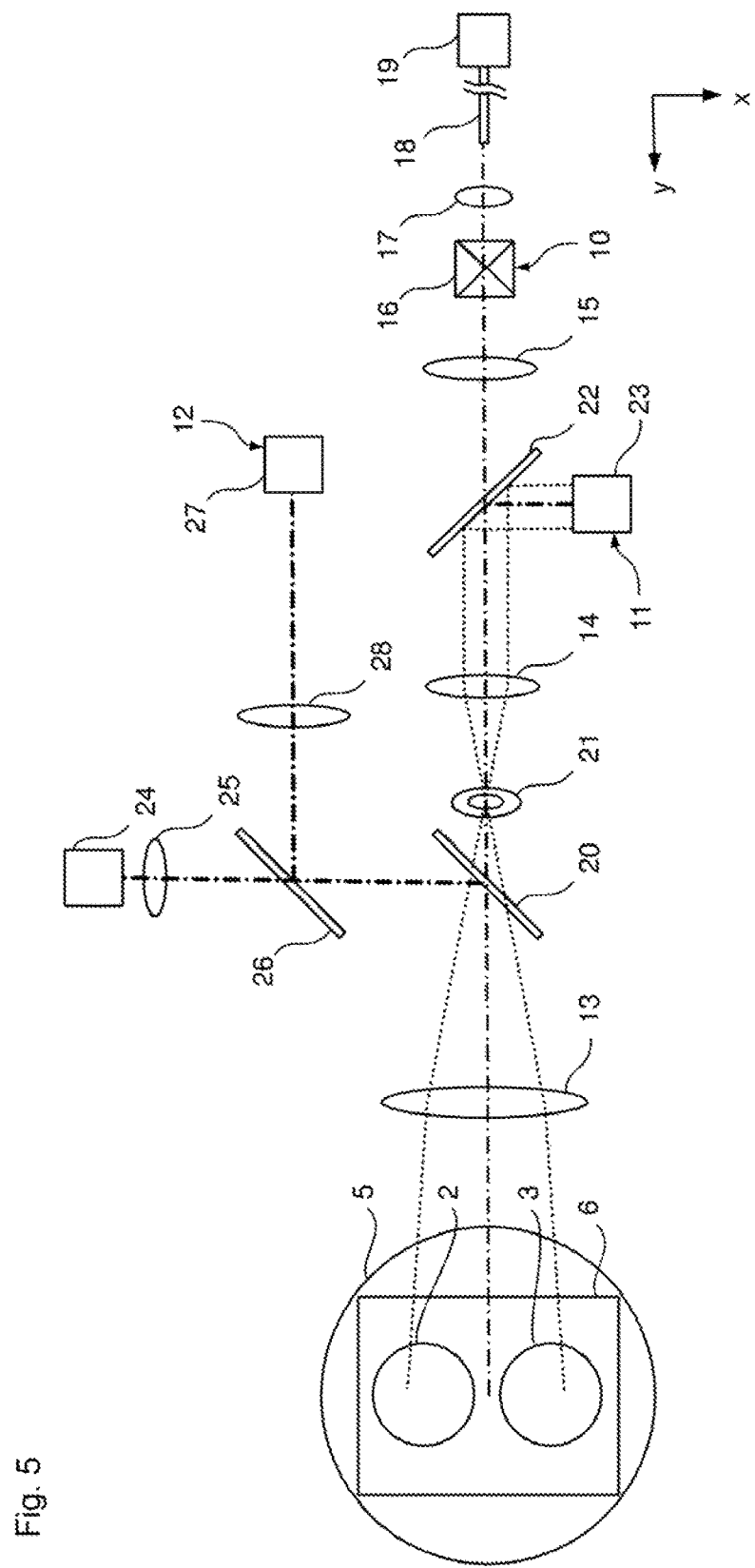
FIG. 5 shows a plan view as per FIG. 2, wherein the detection beam path of the wavefront measuring device is plotted.

The detection beam path of the wavefront measuring device 11 is illustrated schematically in FIG. 5. Here, the main objective 5 and the first optics group 13 form the objective lens of the Kepler telescope and the second optics group 14 forms the eyepiece of the Kepler telescope. Consequently, an afocal imaging optical unit, which is formed by the main objective 5 and the first and second optics group 13 and 14, is also present here. As a result, the object 4 to be examined can be illuminated by a plane wave, which is imaged as a plane wave on the wavefront sensor 23.

As a result of the described optical construction of the two nested Kepler telescopes, an intermediate image ZB (FIG. 4) of the OCT beam path from the object 4 is formed between the second and third optics group 14, 15. This intermediate image ZB is also conjugate to the input into the light guide 18. One could also say that a real intermediate image ZB of the light guide 18 is present, which is conjugate to the object 4. The intermediate image ZB lies closer to the third beam splitter 22 than the second optics group 14 along the optical axis of the Kepler telescope of the OCT device 10. Here, it lies between the third beam splitter 22 and the second optics group 14.

It is advantageous if the intermediate image ZB lies close to the third beam splitter 22 or directly at the position of the third beam splitter 22 since this can minimize a disadvantageous curtailment of the scanning region of the scanning unit 16 of the OCT device 10 by the aperture stop 21 of the wavefront measuring device 11.

The diameter of the intermediate image ZB can lie in the range of 8 to 20 nm, for example.

The first to fourth beam splitters 6, 20, 22 and 26 can be embodied as dichroic beam splitters in each case, which, however, have different dichroic properties.

In order to be able to realize a sufficiently bright illumination with light from the visible wavelength range, which is also referred to as VIS range below and which preferably includes wavelengths from 400 to 700 nm, the reflection for the VIS range at the fourth and second beam splitter 26 and 20 is as high as possible (preferably 100%). The first beam splitter 6 has a reflectivity for the VIS range of 5 to 30% and, correspondingly, a transmission of 95 to 70%. This still ensures that a sufficient amount of illumination light is incident on the object 4 and good optical detection is possible via the two observation beam paths 2, 3.

In order to obtain sufficient illumination for the wavefront measurement, the fourth beam splitter 26 has a transmission that is as high as possible for the wavelength $\lambda_{WFS}$ of the radiation of the illumination laser 24. $\lambda_{WFS}$ can be 785 nm, for example. The second beam splitter 20 has a reflectivity for radiation with the wavelength λWFS in the range of 1 to 10% and a transmission in the range of 99 to 90%. The first beam splitter 6 has a reflectivity for $\lambda_{WFS}$ of preferably 100%. Consequently, although only approximately 1 to 10% of the radiation of the illumination laser 24 is provided for illumination for the wavefront measurement, this is sufficient. The high transmission of the second dichroic beam splitter 20 for the wavelength $\lambda_{WFS}$ in order to lose as little as possible from the return signal that is weak in any case is essential. Since illumination lasers 24 with sufficient power are available, this path can be chosen.

By way of example, if the microscope 1 is used for treatment or operations on the eye, the optical system of the wavefront measuring device 11 can be configured to have a variation in the reflection that is as low as possible since the intensity of the emitted laser radiation must be set for each individual microscope 1 in such a way that the maximum admissible value is not exceeded at the eye to be treated. The lower the relative variation is, the less dynamics the power of the illumination laser 24 must have or the less the illumination laser 24 must be adjusted. By way of example, this means that a transmission of the second beam splitter 20 for the wavelength $\lambda_{WFS}$ of 95±0.5% is better than 99±0.5% since the relative variation of the reflection (R=1−T) is 10% (5%±0.5%) in the first case and 50% (1%±0.5%) in the second case.

Since rectangular spectral curves of the reflection/transmission can only be realized with very high outlay in dichroic beam splitters, this can be used here for the second beam splitter 20 in such a way that $\lambda_{WFS}$ is chosen in such a way that it lies in or at the flank of the spectral increase which reaches its maximum at $\lambda_{OCT}$ (=wavelength of the OCT radiation), where $\lambda_{OCT}$ is, for example, 1050 nm in this case. Hence, the outlay in the layer production can be minimized and the transmission of the second beam splitter 20 is at a maximum at the wavelength of $\lambda_{OCT}$, while it is lower at $\lambda_{WFS}$ and consequently allows input coupling.

The third beam splitter 22 must separate the beam paths of the wavefront measurement and the OCT measurement. Therefore, the third beam splitter 22 has a very high transmission for the wavelength $\lambda_{OCT}$ and reflection that is as high as possible for the wavelength $\lambda_{WFS}$.

Finally, the first beam splitter 6 has a high reflection (preferably 100%) for the wavelength $\lambda_{OCT}$ in order to cause as few losses as possible during the OCT measurement.

Figure 2:
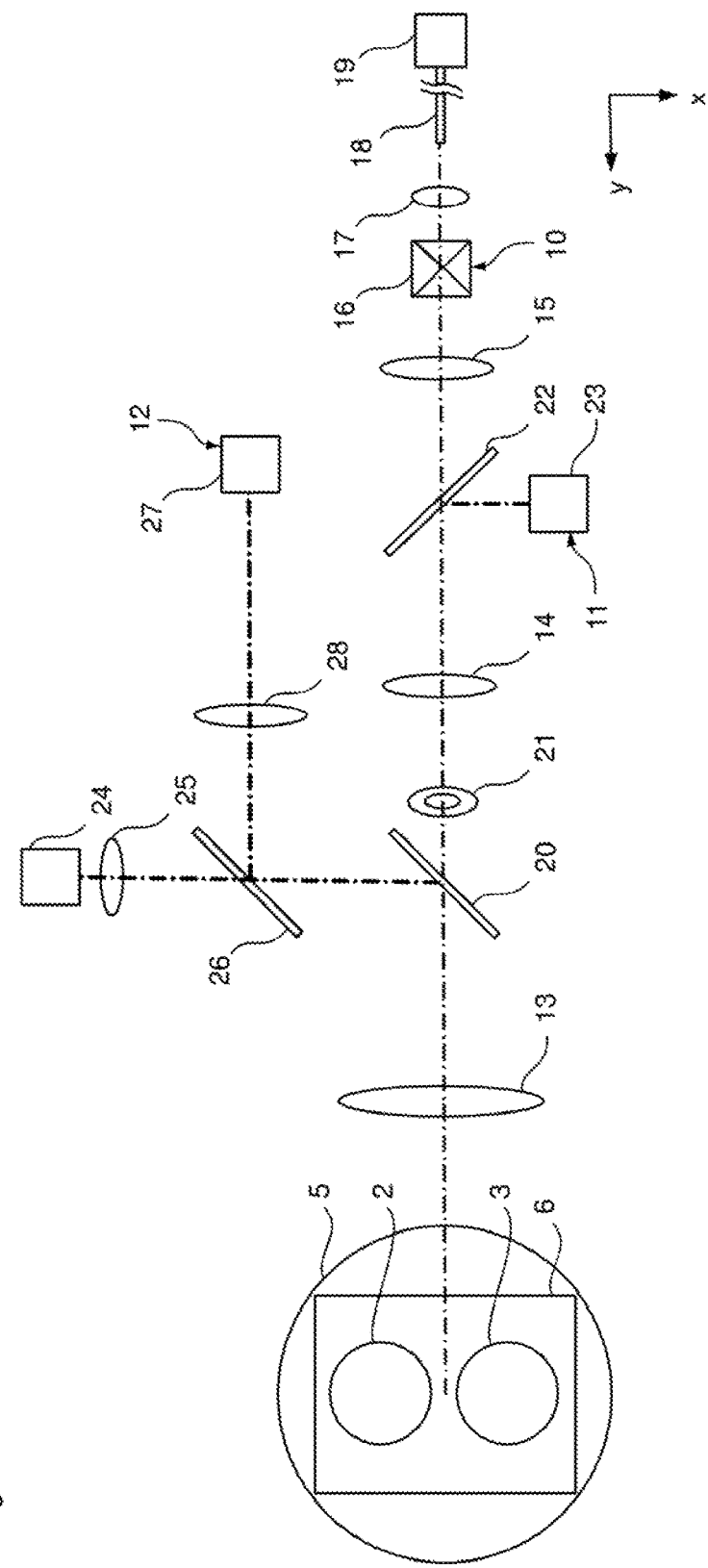
FIG. 2 shows a plan view of the microscope of FIG. 1.
Figure 3:
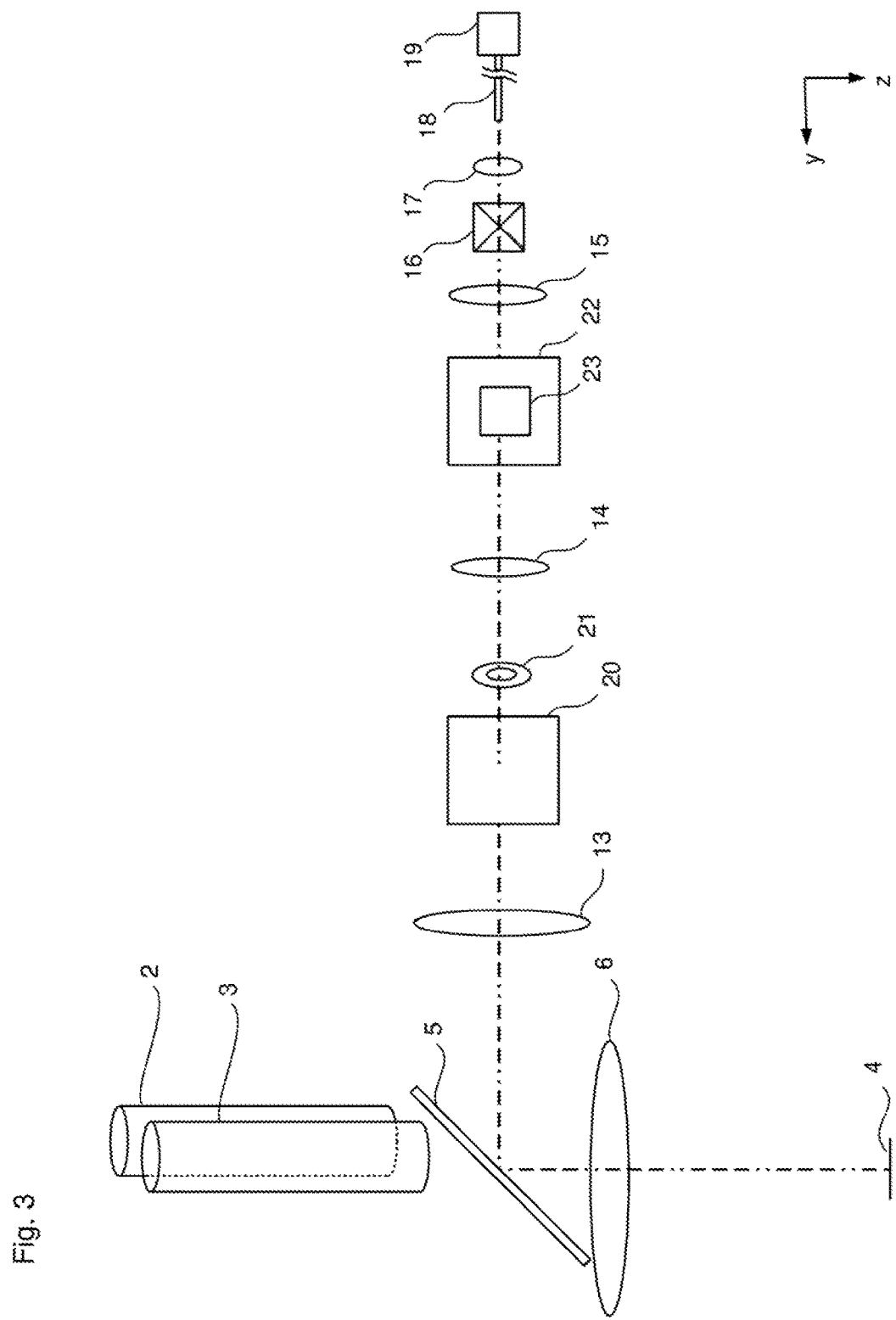
FIG. 3 shows a side view of the microscope of FIG. 1.

As can be gathered, for example, from the illustration in FIG. 2, in particular, the radiation of the illumination laser 24 of the wavefront measuring device 11 is coupled into the beam path of the Kepler telescope of the wavefront measuring device 11 via the second beam splitter 20 such that the radiation of the illumination laser 24 does not run through the second optics group 14 but only through the first optics group 13 and the main objective 5.

Consequently, the light of the wavefront laser 24 only passes through a low number of lenses, as a result of which there is a passage through fewer optical interfaces at which unwanted reflections of the light of the wavefront laser, which may then be incident on the Shack-Hartmann camera 23 in an unwanted manner, may occur.

The third beam splitter 22 can be embodied not only as a dichroic beam splitter, as already described above. By way of example, it is also possible for the third beam splitter 22 to be embodied as a partly transmissive mirror and consequently reflect some of the detection radiation to the Shack-Hartmann camera 23 for the wavefront measurement and transmit some of the measurement radiation to the third optics group 15 for the OCT measurement.

Further, the third beam splitter 22 can be embodied as a mirror which reflects all the radiation incident thereon. For the purposes of transmitting the OCT illumination radiation and OCT measurement radiation, the third beam splitter 22 includes a hole in the region in which the OCT beam path extends. Since the intermediate image ZB lies close to, or directly at, the third beam splitter 22, this hole can be relatively small. The hole can be embodied as a mechanical hole or, for example, as a transparent region that is transmissive to the OCT radiation.

In the previously described embodiments, the third beam splitter 22 was configured in such a way that the wavefront measurement and the OCT measurement can be carried out at the same time. However, if this is not desired and if there should only be provision of the option of carrying out a wavefront measurement and an OCT measurement successively in time, then the third beam splitter 22 can be embodied as a switchable deflection element. The switchable deflection element can be switched from a first state, in which all the light incident on the deflection element is deflected to the Shack-Hartmann camera 23, to a second state, in which no light is deflected but the light can instead continue in unimpeded fashion to the third optics group 15.

To this end, the third beam splitter 22 can include an electrochromic layer or an electrochromic layer system, for example, which is switched into an active state, in which it is strongly reflective, by applying a voltage and which can accordingly be switched into a non-active state (for example, if no voltage is applied), in which it is strongly transmissive.

Figure 6:
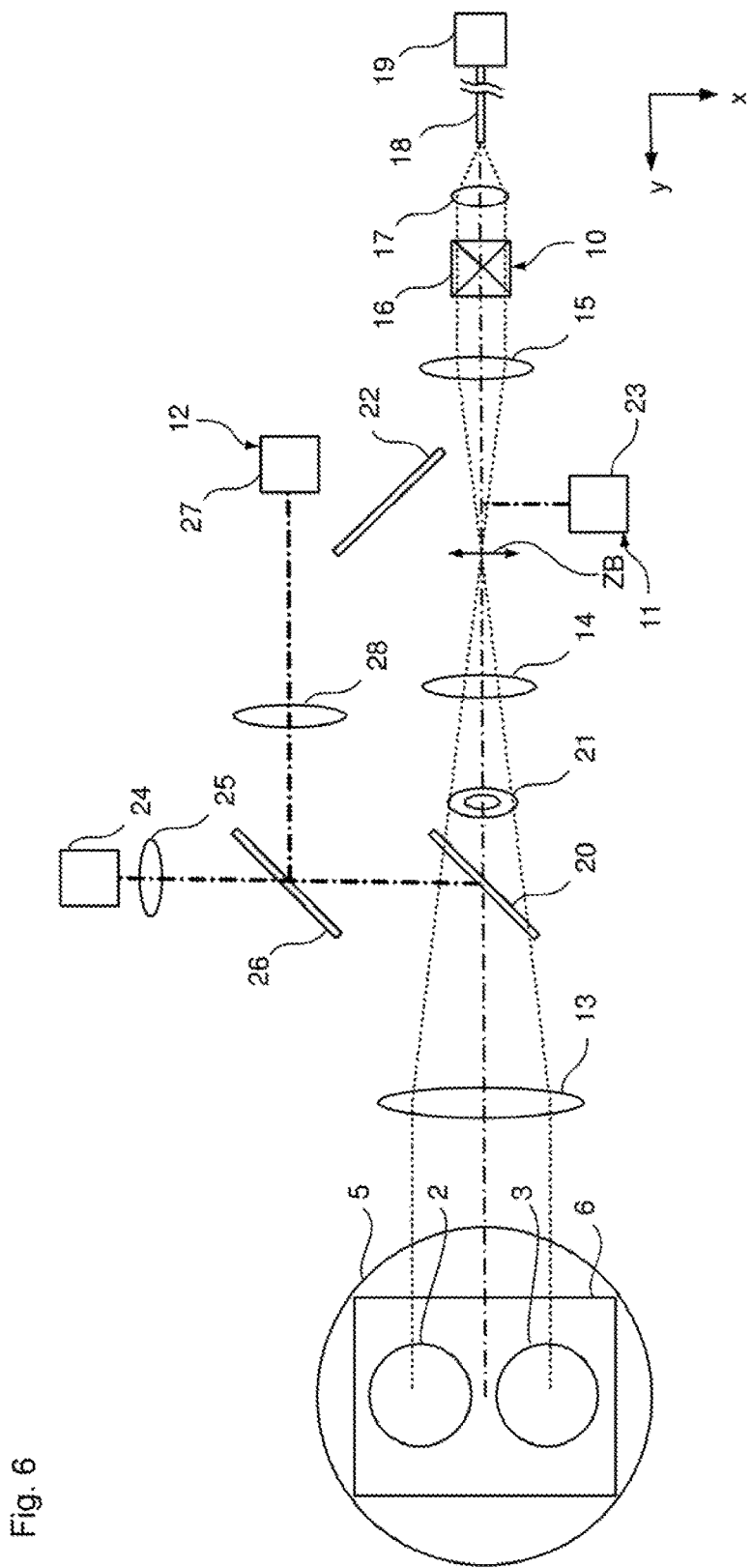
FIG. 6 shows an illustration as per FIG. 4, wherein the third beam splitter 22 is plotted in its second position.

Alternatively, the third beam splitter 22 can be embodied as a mirror which is displaceable from its position shown in FIG. 4 (=first state) to the position shown in FIG. 6 (=second state). The position as per FIG. 6 is outside of the beam path of the OCT device 10 and the wavefront measuring device 11 such that the OCT measurement can be carried out. In the state shown in FIG. 4, all the radiation is deflected to the Shack-Hartmann camera 23 such that the wavefront measurement can be carried out.

In the schematic illustrations as per FIGS. 2 to 6, the first to third optics group 13 to 15 is plotted as a lens in each case. Naturally, each of the optics groups 13 to 15 may contain a plurality of lenses or any other imaging elements.

As already explained above, the intermediate image ZB is in the vicinity or at the location of the third beam splitter 22. As a result of this, component deviations at the third beam splitter 22 or, for example, dirtying of the third beam splitter 22 can influence the OCT measurements in a disadvantageous manner.

Figure 7:
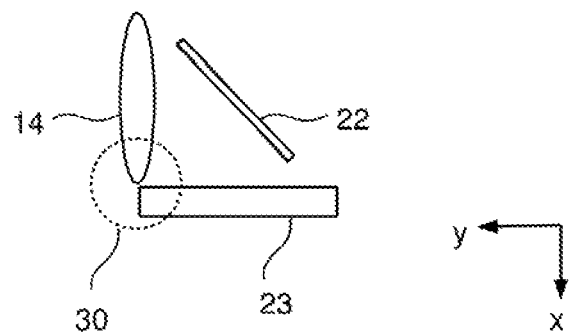
FIG. 7 shows a schematic illustration of the second optics group 14, of the third beam splitter 22 and of the Shack-Hartmann sensor 23 for explaining the spatial proximity of these elements.

Further, the difficulty may occur that the last component of the second optics group 14 only has a relatively small distance (optical path length) from the Shack-Hartmann sensor 23, and so the space between the Shack-Hartmann sensor 23 and the third optics group 15 can become minimal. This is shown schematically in FIG. 7 for the region 30.

Figure 8:
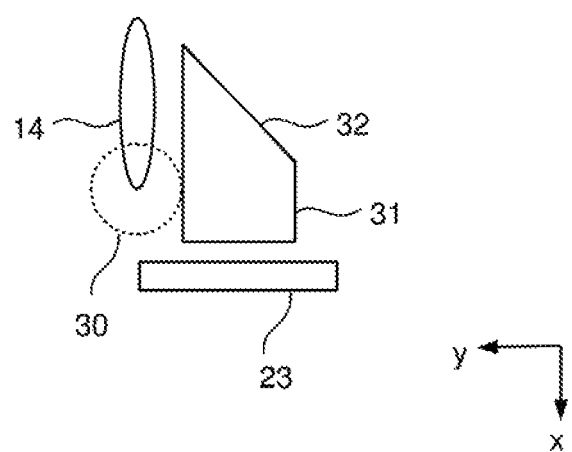
FIG. 8 shows an alternative solution to the arrangement of FIG. 7.

In order to increase the mechanical distance, the third beam splitter 22 can be embodied as a deflection prism 31, as illustrated schematically in FIG. 8. The deflection face 32 can provide the optical properties of the third beam splitter 22.

Since part of the path from the second optics group 14 to the Shack-Hartmann sensor 23 is now no longer passed through in air but in an optically denser medium on account of the deflection prism 31, the desired greater mechanical distance is now present.

The deflection prism 31 can be embodied in such a way that the deflection face 32 carries out beam splitting in order to simultaneously carry out the OCT measurement and the wavefront measurement. Alternatively, the deflection prism 31 can include a purely reflective deflection face 32. In this case, the deflection prism 31 is positioned in the position shown in FIG. 8 in order to carry out the wavefront measurement. If it is not a wavefront measurement but an OCT measurement that should be carried out, the deflection prism 31 is moved out of the beam path (in the same way as the third beam splitter 22 in FIG. 6).

The movement of the third beam splitter 22 or of the deflection prism 31 from the position shown in FIG. 4 and FIG. 8, respectively, into the position shown in FIG. 6 can be realized by a linear movement and/or a pivoting movement (or rotational movement). Preferably, a mechanical stop is provided for the position shown in FIG. 4 or 8 such that the third beam splitter 22 or the deflection prism 31 (or a mount, holder, etc., of the third beam splitter 22 or of the deflection prism 31) only needs to be brought into contact with the stop in order to obtain a positionally accurate and repetition-accurate positioning according to FIG. 4 or 6.

Figure 9:
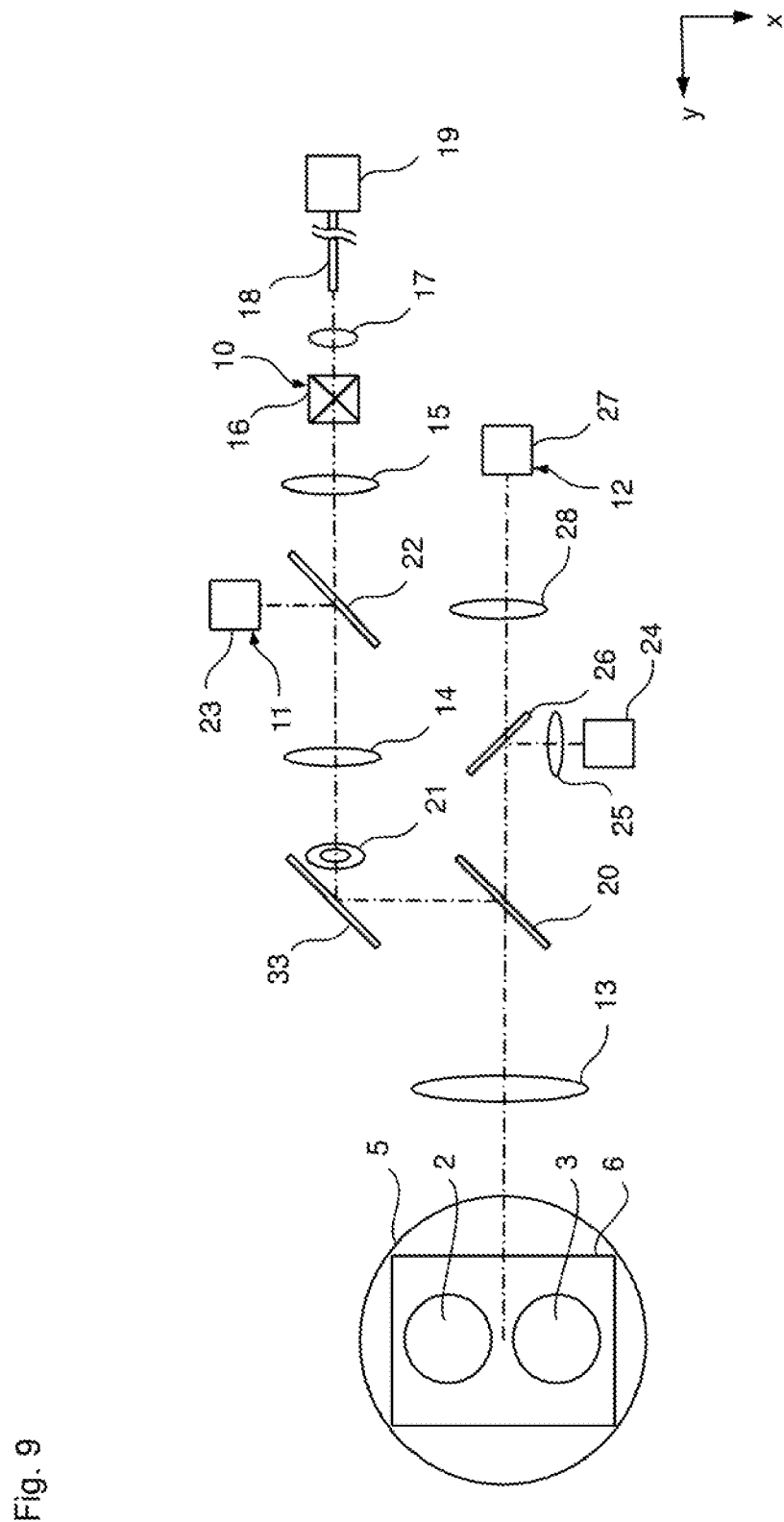
FIG. 9 shows an illustration of a further exemplary embodiment of the microscope according to the invention as per FIG. 2.

In the same way as in FIG. 2, FIG. 9 shows a further embodiment of a microscope 1 according to the invention, in which the spatial arrangement of the OCT device 10, the wavefront device 11 and the illumination device 12 is chosen to be different. However, the same elements are denoted by the same reference signs and, provided nothing else is specified, they have the same properties.

As a result of the modified arrangement, the second beam splitter 22 is embodied in such a way that it has a transmission of 1 to 10% and a reflection of 90 to 99% for radiation with the wavelength $\lambda_{WFS}$. The fourth beam splitter 26 has a transmission of, if possible, 100% for radiation from the range of 400 to 700 nm and a reflection of, if possible, 100% for radiation of the wavelength $\lambda_{WFS}$. Further, the deflection mirror 33 is also provided, the deflection mirror having a reflection of, if possible, 100% for the wavelength $\lambda_{WFS}$ and for the wavelength $\lambda_{OCT}$.

In the previously described embodiments, the third beam splitter 22 always brings about a reflection for detecting the radiation for the wavefront measurement. OCT measurement is carried out in transmission. Naturally, this can also be realized in opposite fashion such that the reflection at the third beam splitter 22 relates to the detection beam path of the OCT measurement and the transmission relates to the wavefront measurement. This interchange between reflection and transmission can also be carried out, for example, for the illumination radiation of the illumination laser 24 and the light source 27.

It is understood that the foregoing description is that of the preferred embodiments of the invention and that various changes and modifications may be made thereto without departing from the spirit and scope of the invention as defined in the appended claims.

The invention claimed is:

1. A microscope comprising:
a main objective;
the microscope defining an observation beam path;
said observation beam path including said main objective;
an [OCT] optical coherence tomography device defining a first detection beam path;
a wavefront measuring device defining a second detection beam path;
a first optics group, a second optics group and a third optics group;
said first detection beam path containing said main objective, said first optics group, said second optics group and said third optics group, wherein said first optics group, said second optics group and said third optics group form an afocal imaging optical unit of said first detection beam path; and,
said second detection beam path containing said main objective, said first optics group and said second optics group, wherein said main objective and said first optics group and said second optics group form an afocal imaging optical unit of said second detection beam path.

2. The microscope of claim 1, wherein:
said first detection beam path has an intermediate image plane; and,
said intermediate image plane lies between said second optics group and said third optics group.

3. The microscope of claim 1 further comprising a first beam splitter, which separates said first detection beam path and said second detection beam path, being arranged between said second optics group and said third optics group.

4. The microscope of claim 2 further comprising a first beam splitter, which separates said first detection beam path and said second detection beam path, being arranged between said second optics group and said third optics group.

5. The microscope of claim 3, wherein said first beam splitter is a dichroic beam splitter.

6. The microscope of claim 4, wherein said first beam splitter is a dichroic beam splitter.

7. The microscope of claim 3, wherein said first beam splitter has a first state and a second state wherein light coming from said second optics group is transmitted in said first detection beam path in said first state of said first beam splitter and transmitted in said second detection beam path in said second state of said first beam splitter.

8. The microscope of claim 4, wherein said first beam splitter has a first state and a second state, wherein light coming from said second optics group is transmitted in said first detection beam path in said first state of said first beam splitter and transmitted in said second detection beam path in said second state of said first beam splitter.

9. The microscope of claim 7, wherein said first beam splitter is configured to deflect light coming from said second optics group in one of said first state and said second state and lets light coming from said second optics group pass in an unimpeded manner in the other one of said first state and said second state.

10. The microscope of claim 8, wherein said first beam splitter is configured to deflect light coming from said second optics group in one of said first state and said second state and lets light coming from said second optics group pass in an unimpeded manner in the other one of said first state and said second state.

11. The microscope of claim 7, wherein said first beam splitter is movable and positioned in the beam path between said second optics group and said third optics group in one of said first state and said second state and positioned outside of said beam path between said second optics group and said third optics group in the other one of said first state and said second state.

12. The microscope of claim 8, wherein said first beam splitter is movable and positioned in the beam path between said second optics group and said third optics group in one of said first state and said second state and positioned outside of said beam path between said second optics group and said third optics group in the other one of said first state and said second state.

13. The microscope of claim 9, wherein the first beam splitter is movable and positioned in the beam path between the second and third optics group in one of the two states and positioned outside of the beam path between the second and third optics group in the other of the two states.

14. The microscope of claim 10, wherein the first beam splitter is movable and positioned in the beam path between the second and third optics group in one of the two states and positioned outside of the beam path between the second and third optics group in the other of the two states.

15. The microscope of claim 1 further comprising an aperture stop for the second detection beam path arranged between said first optics group and said second optics group.

16. The microscope of claim 2 further comprising an aperture stop for the second detection beam path arranged between said first optics group and said second optics group.

17. The microscope of claim 1 further comprising a second beam splitter, via which illumination radiation for said wavefront measuring device is input coupled, being arranged between said first optics group and said second optics group, and wherein the illumination radiation is directed at a specimen to be examined by the microscope via said first optics group and said main objective.

18. The microscope of claim 2 further comprising a second beam splitter, via which illumination radiation for said wavefront measuring device is input coupled, being arranged between said first optics group and said second optics group, and wherein the illumination radiation is directed at a specimen to be examined by the microscope via said first optics group and said main objective.

19. The microscope of claim 1, further comprising an illumination device defining an illumination beam path, wherein said illumination beam path contains said first optics group and said main objective.

20. The microscope of claim 2, further comprising an illumination device defining an illumination beam path, wherein said illumination beam path contains said first optics group and said main objective.

* * * * *